US010143435B2

United States Patent
Hosoki et al.

(10) Patent No.: US 10,143,435 B2
(45) Date of Patent: Dec. 4, 2018

(54) RADIATION IMAGING SYSTEM AND RADIATION IMAGING CONTROL DEVICE

(71) Applicant: Konica Minolta, Inc., Tokyo (JP)

(72) Inventors: Tetsu Hosoki, Koganei (JP); Tsuyoshi Haraguchi, Hino (JP); Kenroku Ubukata, Hachioji (JP)

(73) Assignee: Konica Minolta, Inc., Tokyo (JP)

( * ) Notice: Subject to any disclaimer, the term of this patent is extended or adjusted under 35 U.S.C. 154(b) by 240 days.

(21) Appl. No.: 15/189,712

(22) Filed: Jun. 22, 2016

(65) Prior Publication Data

US 2017/0014093 A1    Jan. 19, 2017

(30) Foreign Application Priority Data

Jul. 17, 2015    (JP) .................. 2015-143371

(51) Int. Cl.
| | |
|---|---|
| *A61B 6/00* | (2006.01) |
| *H04N 5/232* | (2006.01) |
| *H05G 1/62* | (2006.01) |
| *H04N 5/77* | (2006.01) |
| *H04N 5/32* | (2006.01) |

(52) U.S. Cl.
CPC .............. *A61B 6/54* (2013.01); *A61B 6/486* (2013.01); *A61B 6/5217* (2013.01); *A61B 6/541* (2013.01); *H04N 5/23216* (2013.01); *H04N 5/23222* (2013.01); *H04N 5/32* (2013.01); *H04N 5/77* (2013.01); *H05G 1/62* (2013.01); *A61B 6/463* (2013.01); *A61B 6/5264* (2013.01)

(58) Field of Classification Search
CPC ........... A61B 5/54; A61B 6/541; A61B 6/486; A61B 6/5217; A61B 6/463; A61B 6/5264; A61B 6/54; H04N 5/23222; H04N 5/32; H04N 5/23216; H04N 5/77; H05G 1/62
See application file for complete search history.

(56) References Cited

U.S. PATENT DOCUMENTS

2005/0244044 A1* 11/2005 Inoue .................. A61B 6/4233
382/132

FOREIGN PATENT DOCUMENTS

| EP | 2769675 A1 | 8/2014 |
|---|---|---|
| EP | 2829231 A1 | 1/2015 |

(Continued)

OTHER PUBLICATIONS

Japanese Office Action and english translation, 2015-143371, dated Nov. 28, 2017.

(Continued)

*Primary Examiner* — Courtney Thomas
(74) *Attorney, Agent, or Firm* — Lucas & Mercanti, LLP (57) ABSTRACT

A radiation imaging system includes an imaging unit, a detection unit, a change determination unit and a control unit. The imaging unit emits radiation and images a dynamic state of a subject, thereby taking a plurality of frame images of the dynamic state of the subject. The detection unit detects the dynamic state of the subject being imaged and generates detection information on the dynamic state. The change determination unit determines whether change of the dynamic state being imaged is within a predetermined range based on the generated detection information. The control unit controls capturing of the taken frame images according to a result of the determination of the change determination unit.

14 Claims, 6 Drawing Sheets

(56) References Cited

FOREIGN PATENT DOCUMENTS

| JP | 2005312776 A | 11/2005 |
| JP | 2008228914 A | 10/2008 |
| WO | 2013058055 A1 | 4/2013 |

OTHER PUBLICATIONS

Extended European Search Report dated Sep. 9, 2016 from corresponding European Application; Application No. 216175846.1-1902; Applicant: Konica Minolta, Inc.; Total of 8 pages.

* cited by examiner

RADIATION IMAGING SYSTEM AND RADIATION IMAGING CONTROL DEVICE

CROSS-REFERENCE TO RELATED APPLICATIONS

This U.S. Patent Application claims a priority under the Paris Convention of Japanese Patent Application No. 2015-143371 filed on Jul. 17, 2015, the entire disclosure of which, including the specification, claims, drawings and abstract, is incorporated herein by reference in its entirety.

1. Field of the Invention

The present invention relates to a radiation imaging system and a radiation imaging control device.

2. Description of the Related Art

There have been attempts to utilize, for diagnosis, a dynamic image of a subject taken with a semiconductor image sensor such as an FPD (Flat Panel Detector) instead of a still image of a subject taken with a film/screen or a photostimulable phosphor plate. More specifically, by making use of high responsivity of a semiconductor image sensor in reading/deleting image data, a dynamic state of a subject is imaged (photographed) by continuously emitting pulsed radiation from a radiation source in sync with timing of image reading/deletion of the semiconductor image sensor and performing imaging multiple times per second. A series of frame images obtained by the imaging are displayed in order, so that a doctor can observe the dynamic state of the subject.

When the dynamic state of a subject is imaged, the dynamic imaging needs to be performed for a period of time which covers the number of cycles of the dynamic state necessary for diagnosis or dynamic analysis. Then, there have been proposed various technologies to determine the proper timing to start imaging (imaging start timing) and the proper timing to end imaging (imaging end timing).

For example, there is described in International Patent Application Publication No. 2013/058055 a technology of detecting cyclic change of a predetermined site of a subject, specifying recommended imaging start timing based on the detection result, and notifying a photographer of the recommended imaging start timing at multiple stages as the recommended imaging start timing approaches.

By the way, as with general radiation imaging, in dynamic imaging too, reduction of the exposure dose to a subject is required. Meanwhile, if a cyclic dynamic state of a subject, for example, respiration in the case of the subject being a chest part, becomes irregular during imaging, images taken by the time may be unsuitable for diagnosis or analysis.

Conventional technologies including the technology described in International Patent Application Publication No. 2013/058055 can notify a photographer of the recommended imaging start timing and imaging end timing, but cannot cope with when the dynamic state of a subject, such as respiration, becomes irregular during imaging. Hence, in the conventional technologies, when such a situation happens, the entire series of image data obtained by imaging needs to be discarded, and re-imaging needs to be performed. This increases the exposure dose to a subject.

BRIEF SUMMARY OF THE INVENTION

Objects of the present invention include preventing increase in the exposure dose to a subject even if the dynamic state of the subject becomes irregular or the like during dynamic imaging.

In order to achieve at least one of the above objects, according to a first aspect of the present invention, there is provided a radiation imaging system including: an imaging unit which emits radiation and images a dynamic state of a subject, thereby taking a plurality of frame images of the dynamic state of the subject; a detection unit which detects the dynamic state of the subject being imaged and generates detection information on the dynamic state; a change determination unit which determines whether change of the dynamic state being imaged is within a predetermined range based on the generated detection information; and a control unit which controls capturing of the taken frame images according to a result of the determination of the change determination unit.

According to a second aspect of the present invention, there is provided a radiation imaging control device which controls an imaging device which emits radiation and images a dynamic state of a subject, thereby taking a plurality of frame images of the dynamic state of the subject, including: a detection unit which detects the dynamic state of the subject being imaged and generates detection information on the dynamic state; a change determination unit which determines whether change of the dynamic state being imaged is within a predetermined range based on the generated detection information; and a control unit which controls capturing of the taken frame images according to a result of the determination of the change determination unit.

BRIEF DESCRIPTION OF THE SEVERAL VIEWS OF THE DRAWING

The present invention is fully understood from the detailed description given hereinafter and the accompanying drawings, which are given byway of illustration only and thus are not intended to limit the present invention, wherein.

DETAILED DESCRIPTION OF THE INVENTION

Hereinafter, embodiments of the present invention are detailed with reference to the drawings. However, the scope of the present invention is not limited to those embodiments or illustrated examples.

First Embodiment

[Configuration of Radiation Imaging System 100]

First, the configuration of a radiation imaging system 100 is described.

Figure 1:
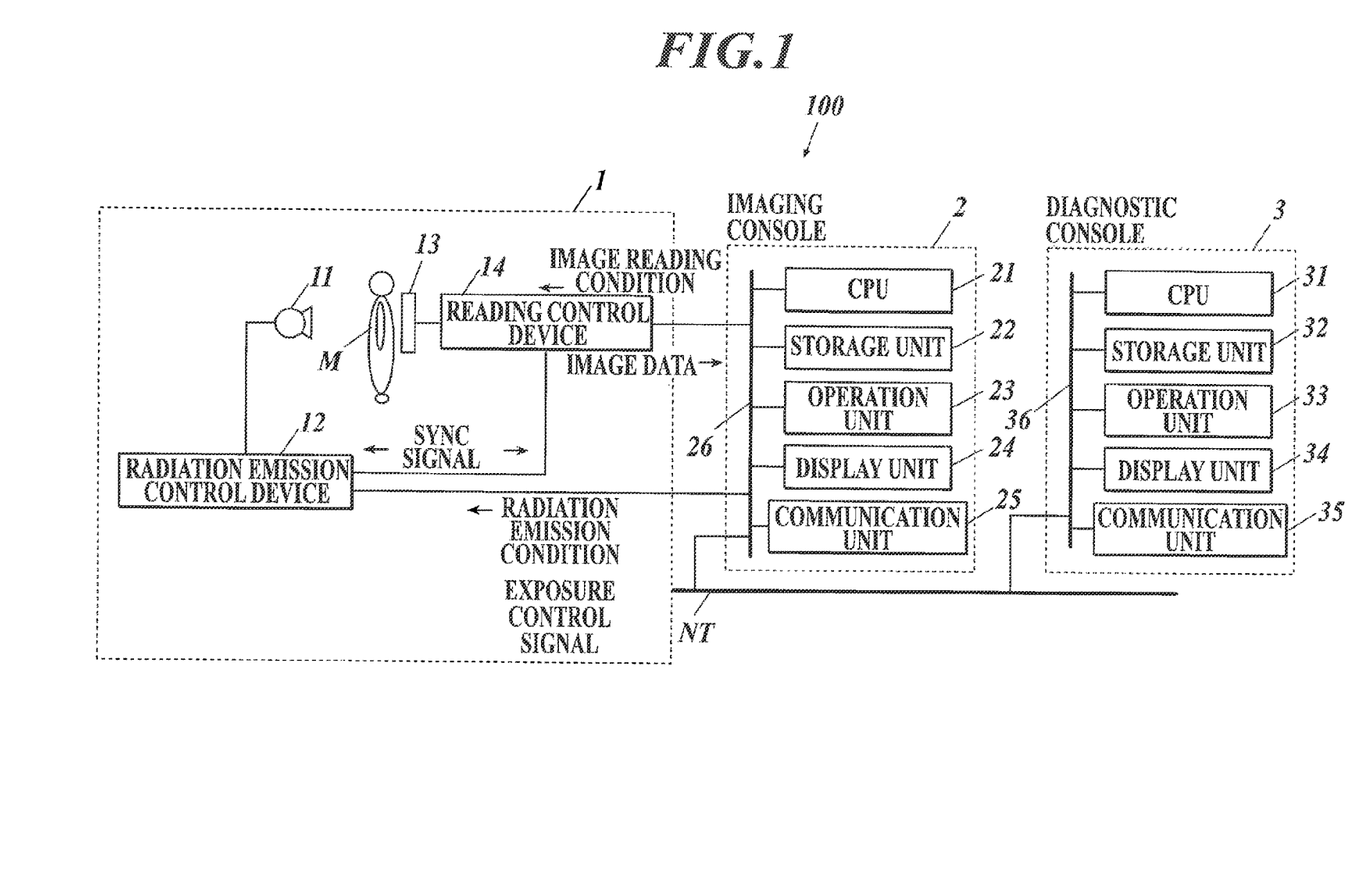
FIG. 1 shows the overall configuration of a radiation imaging system according to embodiments of the present invention.
Figure 2:
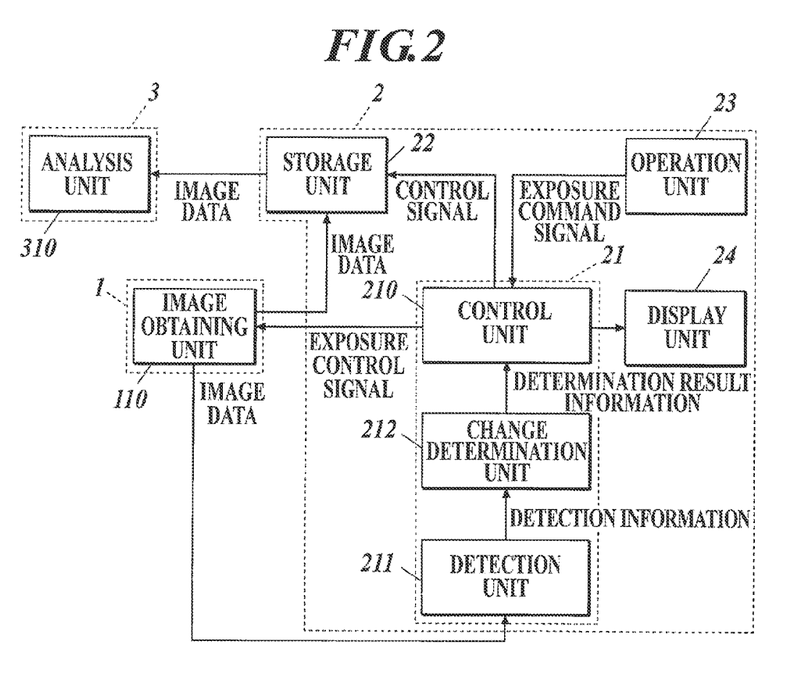
FIG. 2 is a block diagram showing the functional configuration of the radiation imaging system according to first and second embodiments of the present invention.

FIG. 1 shows the overall configuration of the radiation imaging system 100 according to a first embodiment of the present invention. FIG. 2 shows the functional configuration of the radiation imaging system 100 according to the first embodiment of the present invention.

As shown in FIG. 1, the radiation imaging system 100 includes: an imaging device 1; an imaging console 2 connected with the imaging device 1 via a communication cable or the like; and a diagnostic console 3 connected with the imaging console 2 via a communication network NT such as a LAN (Local Area Network). The devices or the like of the radiation imaging system 100 comply with DICOM (Digital Image and Communications in Medicine) standard, and communications between the devices or the like are performed in compliant with DICOM.

[Configuration of Imaging Device 1]

The imaging device 1 functions as an image obtaining unit 110 (imaging unit), and images a cyclic dynamic state of a subject M, thereby obtaining a dynamic image showing the dynamic state of the subject M. Examples of the cyclic dynamic state include: shape change of the lung, i.e., expansion and contraction of the lung, accompanying respiration (respiratory movement); and pulsation of the heart. Dynamic imaging is performed by continuously emitting radiation such as X-rays to a subject M, thereby obtaining a plurality of images of the subject M (hereinafter called "continuous imaging"). A series of images obtained by this continuous imaging is called a dynamic image. Images constituting a dynamic image are called frame images. The subject M is not particularly limited. In the embodiment, the subject M is a chest part.

The imaging device 1 includes, as shown in FIG. 1, a radiation source 11, a radiation emission control device 12, a radiation detection unit 13 and a reading control device 14.

The radiation source 11 is disposed to face the radiation detection unit 13 having a subject M in between, and emits radiation (X-rays) to the subject M under the control of the radiation emission control device 12.

The radiation emission control device 12 is connected with the imaging console 2, and controls the radiation source 11 based on radiation emission conditions input from the imaging console 2 so as to perform radiation imaging. The radiation emission conditions input from the imaging console 2 include a pulse rate, a pulse width and a pulse interval at the time of continuous emission, the number of frames (frame images) to be taken by one imaging, a value of current of an X-ray tube, a value of voltage of the X-ray tube, and a type of an added filter. The pulse rate is the number of times that radiation is emitted per second and matches the frame rate described below. The pulse width is a period of time for one radiation emission. The pulse interval is a period of time from the start of one radiation emission to the start of the next radiation emission in the continuous imaging and matches the frame interval described below.

The radiation detection unit 13 is constituted of a semiconductor image sensor such as an FPD. The FPD is constituted of detection elements (pixels) arranged in a matrix (two-dimensionally) at a predetermined point on a substrate such as a glass substrate. The detection elements detect radiation (intensity of radiation) emitted from the radiation source 11 and passing through at least a subject M, convert the detected radiation into electric signals, and accumulate the electric signals therein. The pixels are provided with switching elements such as TFTs (Thin Film Transistors). There are an indirect conversion type FPD which converts X-rays into electric signals with photoelectric conversion elements via scintillators and a direct conversion type FPD which directly converts X-rays into electric signals. Either of them can be used.

The radiation detection unit 13 is disposed to face the radiation source 11 having a subject M in between.

The reading control device 14 is connected with the imaging console 2. The reading control device 14 controls the switching elements of the pixels of the radiation detection unit 13 based on image reading conditions input from the imaging console 2 to switch the pixels to read the electric signals accumulated in the pixels, thereby reading the electric signals accumulated in the radiation detection unit 13 and obtaining image data. This image data is a frame image(s). The reading control device 14 outputs the obtained frame images to the imaging console 2. The image reading conditions include a frame rate, a frame interval, a pixel size and an image size (matrix size). The frame rate is the number of frame images obtained per second and matches the pulse rate described above. The frame interval is a period of time from the start of one frame image obtaining action to the start of the next frame image obtaining action in the continuous imaging and matches the pulse interval described above.

The radiation emission control device 12 and the reading control device 14 are connected to each other, and exchange sync signals each other so as to synchronize radiation emission actions with image reading actions.

[Configuration of Imaging Console 2]

The imaging console 2, as a radiation imaging control device, outputs the radiation emission conditions and the image reading conditions to the imaging device 1 so as to control radiation imaging and reading actions of radiation images performed by the imaging device 1 and also control capturing of the frame images of the dynamic image(s) taken by the imaging device 1.

The imaging console 2 includes, as shown in FIG. 1, a CPU (Central Processing Unit) 21, a storage unit 22, an operation unit 23, a display unit 24 and a communication unit 25. These units are connected to one another via a bus 26.

The CPU 21 reads, in response to operations on the operation unit 23, a system program and various process programs stored in the storage unit 22, and performs various processes in accordance with the read programs, and thereby functions as a control unit 210, a detection unit 211 and a change determination unit 212 (shown in FIG. 2), which are described below.

The storage unit 22 is constituted of a nonvolatile semiconductor memory, a hard disk or the like. The storage unit 22 stores therein various programs to be executed by the CPU 21, parameters necessary to perform processes of the programs, data such as process results, and so forth. The storage unit 22 also stores therein the radiation emission conditions and the image reading conditions for dynamic imaging of the chest part. The programs are stored in the form of a computer readable program code(s), and the CPU 21 performs actions in accordance with the program code.

The operation unit 23 includes: a keyboard including cursor keys, number input keys and various function keys; and a pointing device such as a mouse, and outputs command signals input by key operation on the keyboard or mouse operation to the CPU 21. The operation unit 23 may have a touch panel on a display screen of the display unit 24. In this case, the operation unit 23 outputs command signals input via the touch panel to the CPU 21. The operation unit 23 also includes an exposure switch to input exposure command signals (exposure start command signals) and outputs operation signals of the exposure switch to the CPU 21.

The display unit 24 is constituted of a monitor such as an LCD (Liquid Crystal Display) or a CRT (Cathode Ray Tube) and displays thereon commands input from the operation unit 23, data and so forth in accordance with commands of display signals input from the CPU 21.

The communication unit 25 includes a LAN adapter, a modem and a TA (Terminal Adapter) and controls data sending/receiving to/from devices connected to the communication network NT.

[Configuration of Diagnostic Console 3]

The diagnostic control 3 is an image processing device which analyzes the dynamic image(s) sent from the imaging console 2 and displays the analysis result and/or the dynamic image so that a doctor can perform radiographic interpretation and make diagnosis.

The diagnostic console 3 includes, as shown in FIG. 1, a CPU 31, a storage unit 32, an operation unit 33, a display unit 34 and a communication unit 35. These units are connected to one another via a bus 36.

The CPU 31 reads, in response to operations on the operation unit 33, a system program and various process programs stored in the storage unit 32, and performs various processes, including an image analysis process, in accordance with the read programs, and thereby functions as an analysis unit 310 (shown in FIG. 2).

The storage unit 32 is constituted of a nonvolatile semiconductor memory, a hard disk or the like. The storage unit 32 stores therein various programs, including a program for the image analysis process, to be executed by the CPU 31, parameters necessary to perform processes of the programs, data such as process results, and so forth. The programs are stored in the form of a computer readable program code(s), and the CPU 31 performs actions in accordance with the program code.

The operation unit 33 includes: a keyboard including cursor keys, number input keys and various function keys; and a pointing device such as a mouse, and outputs command signals input by key operation on the keyboard or mouse operation to the CPU 31. The operation unit 33 may have a touch panel on a display screen of the display unit 34. In this case, the operation unit 33 outputs command signals input via the touch panel to the CPU 31.

The display unit 34 is constituted of a monitor such as an LCD or a CRT and displays thereon commands input from the operation unit 33, data and so forth in accordance with commands of display signals input from the CPU 31.

The communication unit 35 includes a LAN adapter, a modem and a TA and controls data sending/receiving to/from devices connected to the communication network NT.

[Actions of Radiation Imaging System 100]

Next, a series of actions of the radiation imaging system 100 according to the first embodiment is described with reference to FIGS. 2 to 5. Note that, before the actions described below, the radiation emission conditions have been sent to the radiation emission control device 12, and the image reading conditions have been sent to the reading control device 14. Further, a subject M is already positioned between the radiation source 11 and the radiation detection unit 13.

First, when a photographer presses the exposure switch of the operation unit 23 of the imaging console 2, thereby inputting an exposure command signal (here, an exposure start command signal), the control unit 210 outputs an exposure control signal (here, an exposure start control signal) to the image obtaining unit 110 (the radiation emission control device 12, to be specific).

When receives the exposure start control signal from the control unit 210, the image obtaining unit 110 starts dynamic imaging, thereby successively obtaining frame images. More specifically, the radiation source 11 emits radiation to a subject M at pulse intervals set in the radiation emission control device 12, and the radiation detection unit 13 successively obtains frame images. Each time the image obtaining unit 110 obtains a frame image, the image obtaining unit 110 sends image data of the obtained frame image to the imaging console 2.

Each time the control unit 210 receives the image data of the frame image from the image obtaining unit 110, the control unit 210 correlates and stores the received image data with a frame number in the storage unit 22, and also outputs the image data correlated with the frame number to the detection unit 211 in real time.

Each time the detection unit 211 receives the image data of the frame image, the detection unit 211 detects the dynamic state of the subject M based on the received image data, generates detection information on the dynamic state and correlates and outputs the detection information with the frame number to the change determination unit 212 in real time.

In a dynamic image of a chest part, the shape of the lung cyclically (sinusoidally) changes accompanying respiration. One cycle of respiration (one respiratory cycle) is composed of one inhalation mode and one exhalation mode. The inhalation mode is a mode to breathe in. As breath is taken in, the lung field region becomes larger, the diaphragm is pressed (moves) downward, and the density of the lung field becomes lower. The exhalation mode is a mode to breathe out. As breath is given out, the lung field region becomes smaller, the diaphragm moves upward, and the density of the lung field becomes higher.

Figure 3:
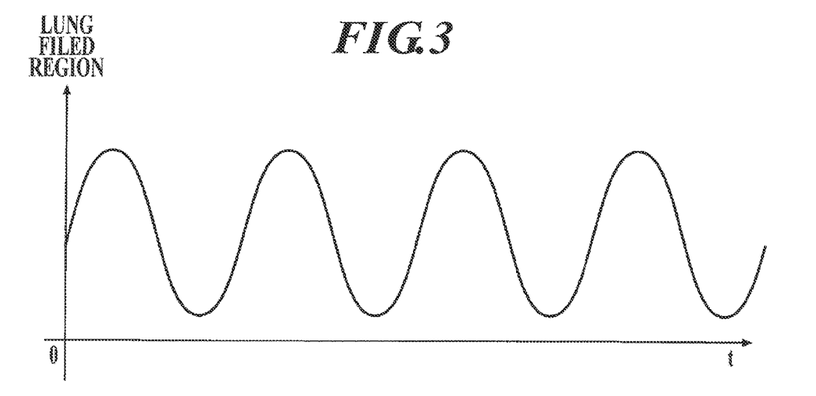
FIG. 3 is a graph (waveform) of the area (or signal value) of a lung field in a dynamic image plotted on the vertical axis over elapsed time t on the horizontal axis.

As the size of the lung field region changes by respiration, in the dynamic image, the area of the lung field becomes larger in the inhalation mode whereas the area of the lung field becomes smaller in the exhalation mode. As the density of the lung field changes by respiration, in the dynamic image, the signal value (density value) of the lung field becomes higher in the inhalation mode whereas the signal value of the lung field becomes lower in the exhalation mode. FIG. 3 is a graph (waveform) of the area (or signal value) of the lung field in a dynamic image obtained by the image obtaining unit 110 plotted on the vertical axis over elapsed time t on the horizontal axis.

The detection unit 211 calculates, for example, the area of the lung field from the received image data of the frame image, and outputs the calculated value of the area of the lung field to the change determination unit 212 as detection information (detected value) on the dynamic state of the subject M.

In order to extract the lung field region from frame image(s), for example, a threshold value is obtained from a histogram of signal values of pixels of frame image(s) by discriminant analysis, and a region having a higher signal value(s) than the threshold value is extracted as a lung field region candidate. Next, edge detection is performed on around the border of the extracted lung field region candidate, and, in small blocks around the border, points where the edge is the maximum are extracted along the border, whereby the border of the lung field region is extracted. The area of the lung field can be calculated based on the number of pixels in the lung field region. Alternatively, the length from the upper end and the lower end of the lung field region may be treated as the area of the lung field.

Instead of the area of the lung field, the average value of signal values of an ROI (Region of Interest) in the lung field region may be calculated as detection information.

Each time the change determination unit 212 receives the detection information from the detection unit 211, the change determination unit 212 determines whether change of the dynamic state of the subject M is within a predetermined range based on the received detection information in real time. More specifically, the change determination unit 212 determines whether phase change of the received detection information is within a predetermined range. Then, the change determination unit 212 correlates and outputs determination result information indicating the determination result with the frame number of the frame image, based on which the detection information used for the determination has been calculated, to the control unit 210.

As described above, the shape of the lung field sinusoidally changes by respiration. With this, the area (or signal value) of the lung field in a dynamic image sinusoidally changes as shown in FIG. 3.

A sine (sinusoidal) wave is expressed by the following Formula 1.

$$y(t)=A\sin(\omega t+\alpha) \quad \text{[Formula 1]}$$

In Formula 1, A represents the amplitude, ω represents the angular frequency, α represents the initial phase, and (ωt+α) represents the phase. The phase is a relative position in one cycle of cyclic movement, in the embodiment, respiration composed of exhalation and inhalation. If a phase is θ, a phase θ+2nπ (n is an arbitrary integer) is defined as θ (the same phase as θ). Under the regular respiration, ω is approximately constant, and the phase changes a certain amount (ω) when time t changes 1.

If a patient chokes or the like during dynamic imaging, his/her respiration becomes irregular and becomes rapid or slow. This irregular respiration does not show change of the lung field due to the patient's normal respiration, and therefore frame images (dynamic image) taken during such irregular respiration are unsuitable for diagnosis or analysis.

When respiration becomes irregular, the speed of shape change of the lung filed changes. That is, phase change in a predetermined period of time different from that under the regular respiration appears. Similarly, in a dynamic image, when respiration becomes irregular, the speed of the area (or signal value) change of the lung field changes. That is, phase change different from that under the regular respiration appears.

Hence, in the embodiment, the change determination unit 212 calculates the change amount (change of the speed) of the detected value, detected by the detection unit 211, per unit time (predetermined time), and determines whether phase change of the dynamic state of the subject M is within a predetermined range based on the calculated change amount.

Figure 4:
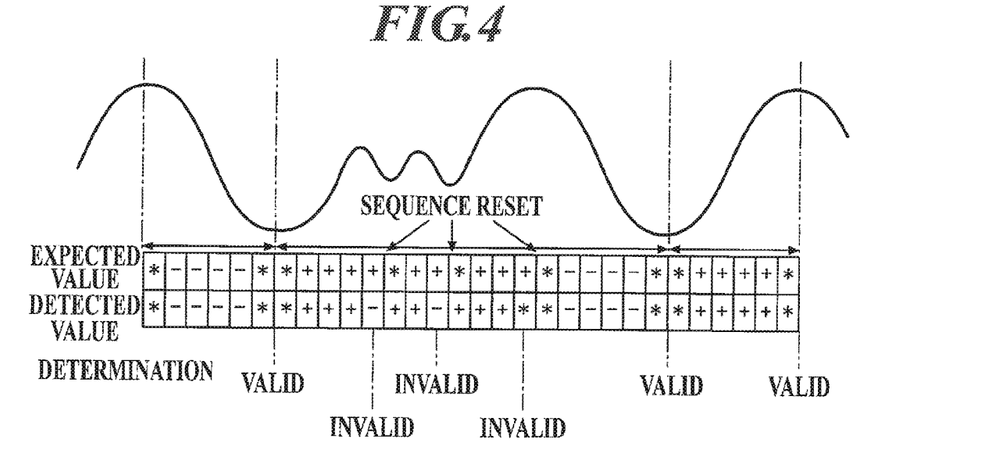
FIG. 4 schematically shows a determination algorithm employed by a change determination unit.

FIG. 4 schematically shows a determination algorithm employed by the change determination unit 212. In FIG. 4, the waveform represents a graph of a detection signal waveform (respiratory waveform) of the detected value on the vertical axis over elapsed time t on the horizontal axis. In the columns of the expected value and the detected value displayed in relation to the horizontal axis of the graph, "+" represents the change amount (the change amount of the expected value or the detected value) at the time being increase by a predetermined reference value or more, "−" represents the change amount at the time being decrease by the reference value or more, and "*" represents the change amount at the time being increase or decrease by less than the reference value. These three types of symbol, "+", "−" and "*", in the columns of the expected value shown in FIG. 4 are symbols to classify, in an expected respiratory waveform (reference respiratory waveform), the change amount of the expected value of the area (signal value) of the lung field per unit time (here, per frame interval). In the embodiment, a pattern composed of one "*" as an initial value which is followed by four continuous "+" or "−" and then followed by one "*" is an expected reference sequence for a half cycle of the dynamic state.

As shown in FIG. 4, the change determination unit 212 determines under which one of the three types of symbol, "+" "−" and "*", the change amount of the detected value per unit time (per frame interval) (here, a difference value between an input detected value and a detected value input one before this input detected value) falls. The change determination unit 212 determines that phase change of the dynamic state is valid (phase change is within a predetermined range) when the symbols representing the change amount of the detected value and the symbols representing the change amount of the expected value match for a half cycle in a row, and determines that phase change of the dynamic state is invalid (phase change is not within the predetermined range) when the symbol representing the change amount of the detected value and the symbol representing the change amount of the expected value do not match, and outputs determination result information indicating the determination result to the control unit 210. The phase change determined to be valid is phase change within a valid range for diagnosis or analysis, and the phase change determined to be invalid is phase change outside the valid range for diagnosis or analysis. When determines that phase change of the dynamic state is invalid, the change determination unit 212 resets the reference sequence, determines the reference sequence depending on whether the detected value in the first period after the sequence reset increases or decreases, and repeats comparison of the change amount of the detected value with the change amount of the expected value.

When receives the determination result information from the change determination unit 212, the control unit 210 controls capturing of the frame image(s) according to the determination result.

Figure 5:
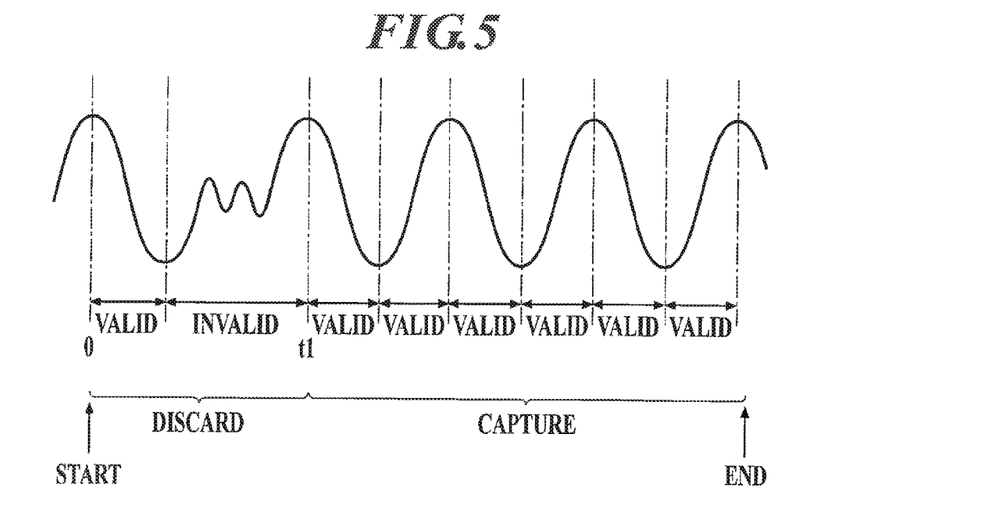
FIG. 5 shows an example of image capturing control performed by a control unit according to the first embodiment.

More specifically, as shown in FIG. 5, when the change determination unit 212 determines during dynamic imaging that phase change of the dynamic state is invalid, the control unit 210 discards (deletes) up to a frame image, stored in the storage unit 22, corresponding to a phase of the dynamic state, the phase being determined by the change determination unit 212 that phase change of the dynamic state is invalid, and stores (captures), in the storage unit 22, frame images corresponding to phases of the dynamic state, the phases being determined by the change determination unit 212 that phase change of the dynamic state is valid.

For example, in FIG. 5, frame images (sequential frame images) from the start of dynamic imaging to immediately before time t1 are discarded (deleted from the storage unit 22), and frame images from time t1 and after that are stored in the storage unit 22.

When a complete set of frame images for a predetermined phase width (a predetermined number of cycles) is present in the storage unit 22, the control unit 210 outputs an exposure end control signal to the image obtaining unit 110, thereby ending dynamic imaging. When instructed (receives a command) to move to the next step (dynamic analysis) from the operation unit 23, the control unit 210 reads this complete set of frame images stored in the storage unit 22 and sends the read frame images to the analysis unit 310 (diagnostic console 3) through the communication unit 25. The analysis unit 310 performs dynamic analysis based on the received frame images of the dynamic image.

According to the first embodiment, a dynamic image composed of only frame images valid for diagnosis or analysis obtained by one dynamic imaging can be captured. This can save the trouble of re-imaging. Further, even if the dynamic state becomes irregular during dynamic imaging, frame images corresponding to phases of the dynamic state, the phases being determined that phase change of the dynamic state is valid, can be used. This can prevent increase in the exposure dose to a patient.

Second Embodiment

Next, a second embodiment of the present invention is described.

The overall configuration of the radiation imaging system 100 of the second embodiment is the same as that described in the first embodiment with reference to FIG. 1, and therefore descriptions thereof are omitted here. Further, the functional configuration of the radiation imaging system. 100 of the second embodiment is the same as that described in the first embodiment with reference to FIG. 2, except the control performed by the control unit 210 according to the determination result of the change determination unit 212. Hereinafter, a series of actions of the radiation imaging system 100 according to the second embodiment is described with reference to FIGS. 2 and 6.

First, when a photographer presses the exposure switch of the operation unit 23 of the imaging console 2, thereby inputting an exposure command signal (here, an exposure start command signal), the control unit 210 outputs an exposure control signal (here, an exposure start control signal) to the image obtaining unit 110 (the radiation emission control device 12, to be specific).

When receives the exposure start control signal from the control unit 210, the image obtaining unit 110 starts dynamic imaging, and each time the image obtaining unit 110 obtains a frame image, the image obtaining unit 110 sends image data of the obtained frame image to the imaging console 2.

Each time the control unit 210 receives the image data of the frame image from the image obtaining unit 110, the control unit 210 correlates and stores the received image data with a frame number in the storage unit 22, and also outputs the image data correlated with the frame number to the detection unit 211 in real time.

Each time the detection unit 211 receives the image data of the frame image, the detection unit 211 detects the dynamic state of the subject M based on the received image data, generates detection information on the dynamic state and correlates and outputs the detection information with the frame number to the change determination unit 212 in real time. An example of the detection unit 211 of the second embodiment is the same as that described in the first embodiment, and therefore descriptions thereof are omitted here.

Each time the change determination unit 212 receives the detection information from the detection unit 211, the change determination unit 212 determines whether change of the dynamic state of the subject M is within a predetermined range based on the received detection information in real time. More specifically, the change determination unit 212 determines whether phase change of the received detection information is within a predetermined range. Then, the change determination unit 212 correlates and outputs determination result information indicating the determination result with the frame number of the frame image, based on which the detection information used for the determination has been calculated, to the control unit 210. An example of the determination algorithm employed by the change determination unit 212 of the second embodiment is the same as that described in the first embodiment, and therefore descriptions thereof are omitted here.

When receives the determination result information from the change determination unit 212, the control unit 210 controls capturing of the frame image(s) according to the determination result.

Figure 6:
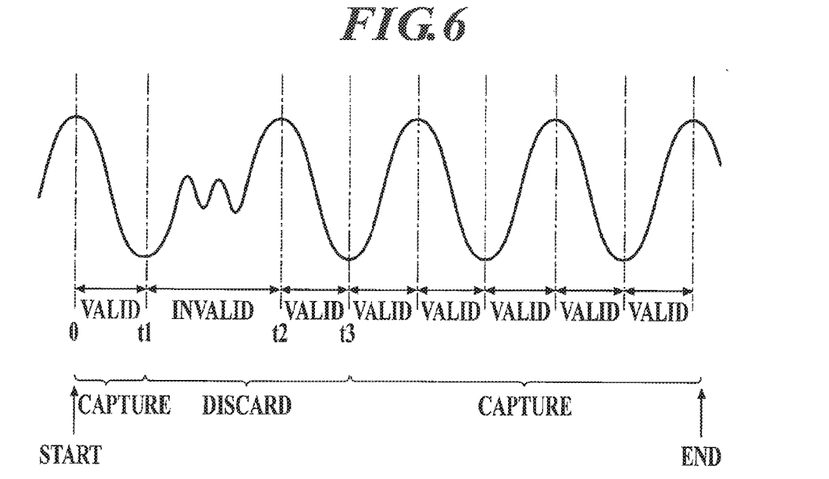
FIG. 6 shows an example of image capturing control performed by the control unit according to the second embodiment.

More specifically, as shown in FIG. 6, when the change determination unit 212 determines during dynamic imaging that phase change of the dynamic state is invalid, the control unit 210 discards (deletes), stored in the storage unit 22, a frame image(s) corresponding to a phase(s) of the dynamic state, the phase(s) being determined by the change determination unit 212 that phase change of the dynamic state is invalid, and automatically connects (i) a frame image taken (obtained) by the image obtaining unit 110 after the discarded frame image(s), and corresponding to a phase of the dynamic state, the phase (of the phases) being determined by the change determination unit 212 that phase change of the dynamic state is valid and being the same as the phase of the dynamic state corresponding to the discarded frame image, to (ii) a frame image immediately before the discarded frame image(s) so as to follow this frame image immediately before the discarded frame image(s). Frame images determined to be valid but not meeting the condition for the connection (e.g., frame images from time t2 to time t3 in FIG. 6) are discarded.

For example, in FIG. 6, frame images from time t1 to time t3 are discarded, and frame images from time t3 and after that are automatically connected so as to follow a frame image immediately before time t1.

When a complete set of frame images for a predetermined phase width (a predetermined number of cycles) is present in the storage unit 22, the control unit 210 outputs an exposure end control signal to the image obtaining unit 110, thereby ending dynamic imaging. When instructed (receives a command) to move to the next step (dynamic analysis) from the operation unit 23, the control unit 210 reads this complete set of frame images stored in the storage unit 22 and sends the read frame images to the analysis unit 310 (diagnostic console 3) through the communication unit 25. The analysis unit 310 performs dynamic analysis based on the received frame images of the dynamic image.

According to the second embodiment, a dynamic image composed of only frame images valid for diagnosis or analysis obtained by one dynamic imaging can be captured. This can save the trouble of re-imaging. Further, even if the dynamic state becomes irregular during dynamic imaging, frame images corresponding to phases of the dynamic state, the phases being determined that phase change of the dynamic state is valid, can be used. This can prevent increase in the exposure dose to a patient. Further, frame images before the frame image(s) determined to be invalid can also be used. This can further prevent increase in the exposure dose to a patient.

Third Embodiment

Next, a third embodiment of the present invention is described.

In the first and second embodiments, during dynamic imaging, frame images corresponding to phases of the dynamic state, the phases being determined that phase change of the dynamic state is invalid, are discarded, and only frame images corresponding to phases of the dynamic state, the phases being determined that phase change of the dynamic state is valid, are captured, in real time. However, in the third embodiment, after dynamic imaging finishes, frame images corresponding to phases of the dynamic state, the phases being determined that phase change of the dynamic state is valid, are captured in response to a photographer's operation(s). Further, in the first and second embodiments, the control unit 210 automatically ends dynamic imaging. However, in the third embodiment, the control unit 210 ends dynamic imaging when receives an exposure end command signal in response to a photographer's deactivation operation on the exposure switch.

The overall configuration of the radiation imaging system 100 of the third embodiment is the same as that described in the first embodiment with reference to FIG. 1, and therefore descriptions thereof are omitted here. Hereinafter, a series of actions of the radiation imaging system 100 according to the third embodiment is described with reference to FIGS. 7 to 9.

Figure 7:
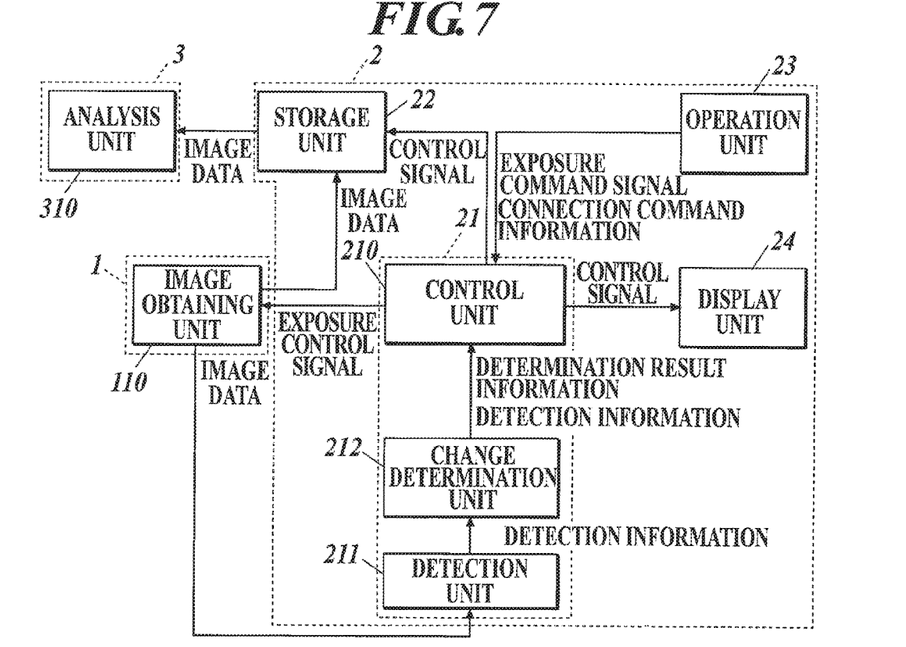
FIG. 7 is a block diagram showing the functional configuration of the radiation imaging system according to a third embodiment of the present invention.

First, when a photographer presses the exposure switch of the operation unit 23 of the imaging console 2, thereby inputting an exposure command signal (here, an exposure start command signal), the control unit 210 outputs an exposure control signal (here, an exposure start control signal) to the image obtaining unit 110 (the radiation emission control device 12, to be specific).

When receives the exposure start control signal from the control unit 210, the image obtaining unit 110 starts dynamic imaging, and each time the image obtaining unit 110 obtains a frame image, the image obtaining unit 110 sends image data of the obtained frame image to the imaging console 2.

Each time the control unit 210 receives the image data of the frame image from the image obtaining unit 110, the control unit 210 correlates and stores the received image data with a frame number in the storage unit 22, and also outputs the image data correlated with the frame number to the detection unit 211 in real time.

Each time the detection unit 211 receives the image data of the frame image, the detection unit 211 detects the dynamic state of the subject M based on the received image data, generates detection information on the dynamic state and correlates and outputs the detection information with the frame number to the change determination unit 212 in real time. An example of the detection unit 211 of the third embodiment is the same as that described in the first embodiment, and therefore descriptions thereof are omitted here.

Each time the change determination unit 212 receives the detection information from the detection unit 211, the change determination unit 212 determines whether change of the dynamic state of the subject M is within a predetermined range based on the received detection information in real time. More specifically, the change determination unit 212 determines whether phase change of the received detection information is within a predetermined range. Then, the change determination unit 212 correlates and outputs determination result information indicating the determination result and the detection information used for the determination with the frame number of the frame image to the control unit 210. An example of the determination algorithm employed by the change determination unit 212 of the third embodiment is the same as that described in the first embodiment, and therefore descriptions thereof are omitted here.

When receives the determination result information and the detection information used for the determination, which are correlated with the frame number, from the change determination unit 212, the control unit 210 stores the received determination result information and detection information correlated with the frame number in the storage unit 22.

Figure 8:
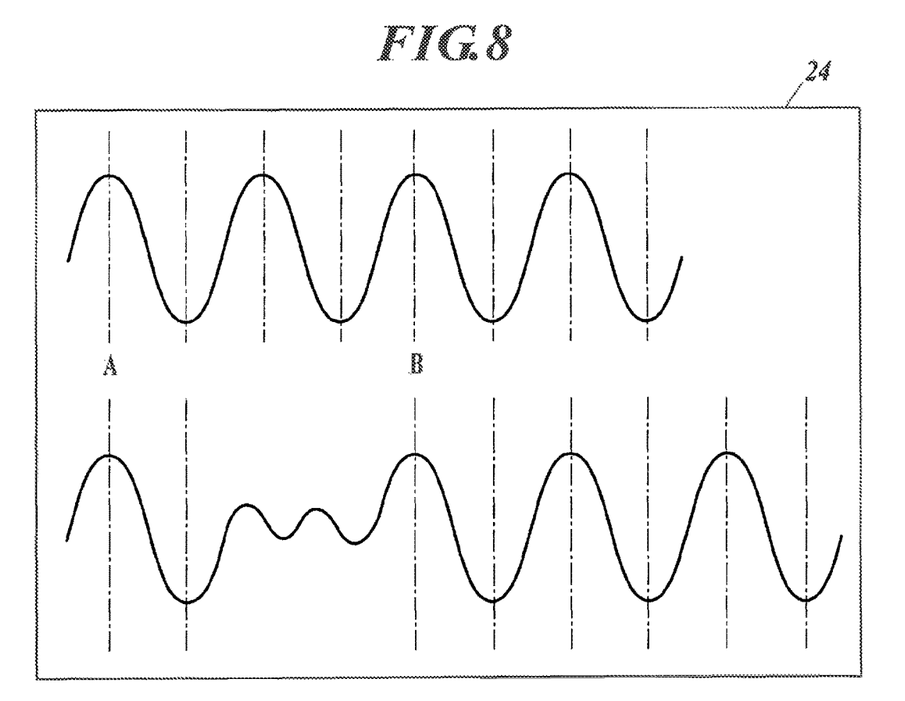
FIG. 8 shows an example of a screen on which the phase width of the dynamic state to be obtained by imaging (reference) and the phase width of the dynamic state of frame images already obtained (taken) by imaging are simultaneously displayed.

Further, the control unit 210 simultaneously displays, during dynamic imaging, the phase width of the dynamic state to be obtained by imaging (reference) and the phase width of the dynamic state of frame images already obtained (taken) by the image obtaining unit 110 on the display unit 24 in order to assist the photographer to catch the imaging end timing. For example, as shown in FIG. 8, the control unit 210 displays the waveform of the phase width of the dynamic state to be obtained (e.g., three cycles of respiration starting from the maximal inspiratory level) at the upper row on the display screen of the display unit 24, and also displays, based on the detection information input from the change determination unit 212, the waveform of the phase width of the dynamic state already obtained by the image obtaining unit 110 at the lower row on the display screen of the display unit 24. This lets the photographer readily catch how much the phase width (valid phase width) of the dynamic state of valid frame images is already obtained with respect to the phase width of the dynamic state to be obtained (i.e., how many valid frame images are already obtained with respect to all frame images to be obtained), namely, readily catch the imaging end timing.

In order to let the photographer more intuitively catch how much the phase width of the dynamic state of valid frame images is already obtained with respect to the phase width of the dynamic state to be obtained, the phase width of the dynamic state to be obtained displayed at the upper row may be shifted to the right according to the already-obtained phase width of the dynamic state displayed at the lower row. For example, in the case shown in FIG. 8, the shifting may be performed such that the position A is to be at the position B. This lets the photographer intuitively catch that dynamic imaging finishes in about a half cycle.

When a complete set of frame images for the whole phase width of the dynamic state to be obtained is not present, the control unit 210 may display, on the display unit 24, information to lead the photographer to keep imaging the dynamic state.

For example, as an indication to lead the photographer to keep imaging the dynamic state, the control unit 210 displays (outputs), on the display unit 24, an obtaining state of valid frame images (frame images determined by the change determination unit 212 that phase change of the dynamic state is valid) with respect to frame images for the whole phase width of the dynamic state to be obtained. More specifically, the control unit 210 displays the waveform of the phase width of the dynamic state to be obtained at the upper row on the display screen of the display unit 24, and also displays, based on the detection information and the determination result information input from the change determination unit 212, the waveform of the phase width of the dynamic state of the already-obtained valid frame images at the lower row on the display screen of the display unit 24. Alternatively or additionally, the control unit 210 may calculate, based on the determination result information input from the change determination unit 212, a ratio (%) of the phase width of the dynamic state of the already-obtained valid frame images to the phase width of the dynamic state to be obtained, and display the calculated ratio on the display unit 24. Alternatively or additionally, the control unit 210 may calculate, based on the phase width of the dynamic state of the already-obtained valid frame images, the number of respirations (breaths) for which valid frame images are already obtained, and display the calculated number of respirations on the display unit 24. Any of these can prevent the photographer from stopping imaging halfway through the end. Further, any of these lets the photographer readily catch how many valid frame images are already obtained with respect to the phase width of the dynamic state to be obtained, or how much more the imaging should be kept. The imaging console 2 may be provided with a sound output unit and/or a vibration generation unit (both not shown) to output sound(s) and/or vibration(s) according the ratio (%) of the phase width of the dynamic state of the already-obtained valid frame images to the phase width of the dynamic state to be obtained (e.g., three cycles of respiration starting from the maximal inspiratory level).

When a complete set of frame images for the whole phase width of the dynamic state to be obtained is present, the control unit 210 may display, on the display unit 24, an indication to notify that the complete set of frame images is present. For example, the control unit 210 displays that the phase width of the dynamic state of the obtained valid frame images has reached 100%, or that the number of respirations has reached a predetermined number of respirations. This lets the photographer catch the imaging end timing (timing to deactivate the exposure switch). The imaging console 2 may be provided with a sound output unit and/or a vibration generation unit (both not shown) to output sound(s) and/or vibration(s) (different from those indicating the obtaining state) indicating that the complete set of frame images is present.

When the photographer deactivates the exposure switch of the operation unit 23, thereby inputting an exposure end command signal, the control unit 210 sends (outputs) an exposure control signal (here, an exposure end control signal) to the image obtaining unit 110 (the radiation emission control device 12, to be specific), thereby ending dynamic imaging.

When dynamic imaging finishes, the control unit 210 reads the series of frame images and the determination result information stored in the storage unit 22, and controls capturing of the frame images according to the determination result information for the respective frame images.

More specifically, when the change determination unit 212 determines that phase change of the dynamic state is invalid (i.e., when the determination result information indicating the determination result of invalid is present), the control unit 210 discards a frame image(s) corresponding to a phase(s) determined by the change determination unit 212 that phase change of the dynamic state is invalid (deletes them from the storage unit 22). Next, the control unit 210 displays, on the display unit 24, a connection command screen to connect the frame images, which become separate by the discarding (deletion), in response to the photographer's connection command operation(s) on the operation unit 23. Then, the control unit 210 connects the frame images other than the discarded frame images (i.e., of the series of frame images taken by dynamic imaging this time, the remaining not-discarded frame images) with each other based on a connection command signal input from the operation unit 23 through the connection command screen, and stores the connected frame images in the storage unit 22 as a dynamic image.

Figure 9:
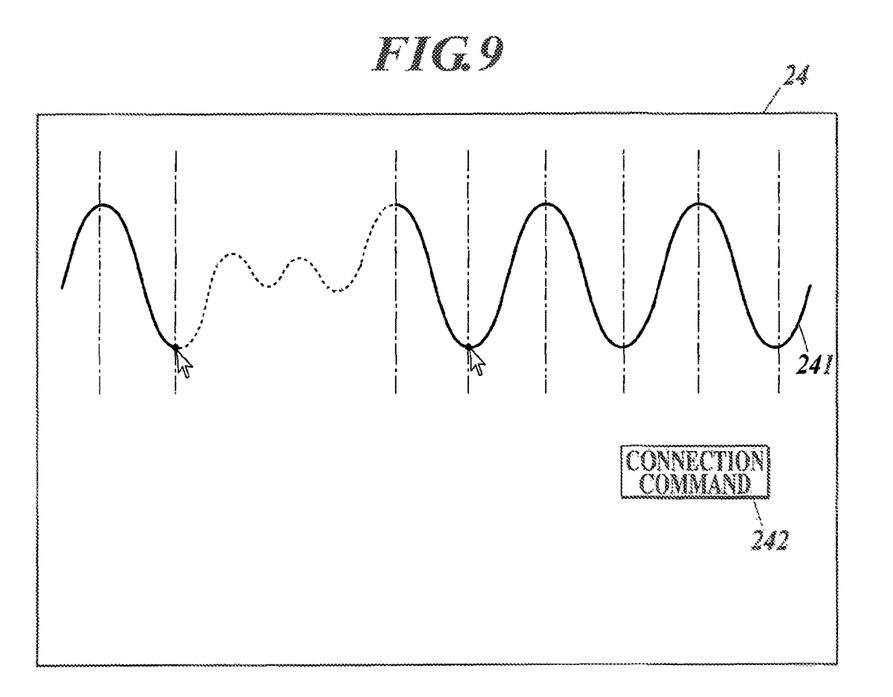
FIG. 9 shows an example of a connection command screen.

For example, the control unit 210 displays the connection command screen on the display unit 24 based on the detection information on the dynamic state stored in the storage unit 22. The connection command screen is, for example, a screen on which a waveform 241 showing the dynamic state during dynamic imaging, a connection command button 242 and so forth are displayed as shown in FIG. 9. In the waveform 241, the discarded phase width is distinguishably displayed. When two points on the waveform are specified and the connection command button 242 is pressed through the operation unit 23, whereby a connection command signal is input, the control unit 210 connects the specified points (i.e., eliminates the space between the frame images of the specified points) in response to the connection command signal, and stores (captures) the connected frame images in the storage unit 22 as a dynamic image. Frame images corresponding to phases between the specified phases (specified points) are discarded.

In the third embodiment, two points on the waveform are specified, and a connection command to connect the specified two points is made. However, by increasing the number of points to specify, a plurality of connection commands to connect the specified more than two points (fragmented frame images) may be made, and the order of the frame images may be changed when the specified points (frame images) are connected.

If no frame images corresponding to phases determined by the change determination unit 212 that phase change of the dynamic state is invalid are present, the control unit 210 captures, as a dynamic image, the frame images stored in the storage unit 22 as they are.

When finishes capturing the frame images, the control unit 210 determines whether a complete set of frame images for the whole phase width of the dynamic state to be obtained is present based on the determination result information. When determines that the complete set of frame images for the whole phase width of the dynamic state to be obtained is not present, the control unit 210 displays on the display unit 24 that proceeding to the next step is unavailable. For example, the control unit 210 displays a message of "Not all necessary images are present. Keep imaging." or the like on the display unit 24. The imaging console 2 may be provided with a not-shown sound output unit to output the message with a voice sound or output a predetermined buzzer sound or the like therefor. Any of these can prevent proceeding to the next step without having a complete set of frame images for the whole phase width of the dynamic state to be obtained, the complete set of frame images being necessary for diagnosis or analysis.

On the other hand, when determines that the complete set of frame images for the whole phase width of the dynamic state to be obtained is present, the control unit 210 waits for a proceeding command to proceed to the next step (dynamic analysis) to be input from the operation unit 23, and when receives the proceeding command, reads the complete set of frame images stored in the storage unit 22 and sends the read frame images to the analysis unit 310 (diagnostic console 3) through the communication unit 25. The diagnostic console 3 performs dynamic analysis based on the received frame images of the dynamic image.

According to the third embodiment, a photographer can manually perform a connection operation of frame images and connect the frame images at the optimum phase while checking the phase to connect. Further, even if the dynamic state becomes irregular during dynamic imaging, frame images corresponding to phases determined that phase change of the dynamic state is valid, can be used. This can prevent increase in the exposure dose to a patient.

In the third embodiment, in order to assist a photographer to catch the imaging end timing, during dynamic imaging, the control unit 210 simultaneously displays the phase width of the dynamic state to be obtained (reference) and the phase width of the dynamic state of frame images already obtained by the image obtaining unit 110 on the display unit 24 or displays the obtaining state of valid frame images on the display unit 24. For these kinds of display, the detection unit 211 detects the dynamic state of a subject M and the change determination unit 212 determines whether change of the cyclic dynamic state is valid in real time during dynamic imaging. However, the above-described display is not essential. If no such display is performed, the detection unit 211 may detect the dynamic state based on each frame image of a series of frame images stored in the storage unit 22 after dynamic imaging finishes, and the change determination unit 212 may determine whether change of the dynamic state is valid or invalid based on the detection information for the respective frame images.

Further, in the third embodiment, after dynamic imaging finishes, the control unit 210 connects frame images before and after the frame images determined by the change determination unit 212 that phase change of the dynamic state is invalid and accordingly discarded, in response to an operation(s) on the operation unit 23. However, this connection in the third embodiment may be performed automatically by the control unit 210. That is, as described in the second embodiment, the control unit 210 may automatically connect (i) a frame image taken (obtained) by the image obtaining unit 110 after the discarded frame image(s), and corresponding to a phase of the dynamic state, the phase being determined by the change determination unit 212 that phase change of the dynamic state is valid and being the same as the phase of the dynamic state corresponding to the discarded frame image, to (ii) a frame image immediately before the discarded frame image(s) so as to follow this frame image immediately before the discarded frame image(s).

As described above, according to the radiation imaging system 100, while the imaging device 1 is imaging a dynamic state of a subject M, thereby taking a dynamic image (frame images) of the subject M, the detection unit 211 detects the dynamic state of the subject M being imaged and generates detection information on the dynamic state; the change determination unit 212 determines whether change of the dynamic state (e.g., phase change of the dynamic state) being imaged is within a predetermined range based on the generated detection information; and the control unit 210 controls capturing of the frame images taken by the imaging device 1 according to the determination result of the change determination unit 212.

Thus, the present invention can control capturing or not capturing of the taken frame images depending on whether change of the dynamic state is within a predetermined range (valid). Therefore, even if the dynamic state of a subject becomes irregular during dynamic imaging, frame images taken while the dynamic state is not irregular can be used. This can prevent increase in the exposure dose to a subject.

For example, when the change determination unit 212 determines that the change of the dynamic state of the subject M is not within the predetermined range, the control unit 210 discards up to a frame image determined by the change determination unit 212 that the change of the dynamic state is not within the predetermined range, and captures a frame image, after the discarded frame image, determined by the change determination unit 212 that the change of the dynamic state is within the predetermined range.

Therefore, even if the dynamic state of a subject becomes irregular during dynamic imaging, frame images taken while the dynamic state is not irregular can be used. This can prevent increase in the exposure dose to a subject. Further, a dynamic image composed of only valid frame images determined that change of the dynamic state is within a predetermined range and obtained by one dynamic imaging can be captured. This can save the trouble of re-imaging.

Further, for example, when the change determination unit 212 determines that the change of the dynamic state of the subject M is not within the predetermined range, the control unit 210 discards a frame image determined by the change determination unit 212 that the change of the dynamic state is not within the predetermined range, and automatically connects (i) a frame image taken by the imaging device 1 after the discarded frame image, determined by the change determination unit 212 that the change of the dynamic state is within the predetermined range, and corresponding to a phase of the dynamic state, the phase being the same as a phase of the dynamic state corresponding to the discarded frame image, to (ii) a frame image immediately before the discarded frame image.

Therefore, even if the dynamic state of a subject becomes irregular during dynamic imaging, frame images taken while the dynamic state is not irregular can be used. This can prevent increase in the exposure dose to a subject. Further, a dynamic image composed of only valid frame images determined that change of the dynamic state is within a predetermined range and obtained by one dynamic imaging can be captured. This can save the trouble of re-imaging. Further, frame images taken before the dynamic state becomes irregular can also be used. This can further prevent increase in the exposure dose to a subject.

Further, for example, when the change determination unit 212 determines that the change of the dynamic state of the subject M is not within the predetermined range, the control unit 210 discards a frame image determined by the change determination unit 212 that the change of the dynamic state is not within the predetermined range, and connects, based on the connection command information input from the operation unit 23, frame images other than the discarded frame image.

This lets a photographer manually perform a connection operation of frame images and connect the frame images at the optimum phase while checking the phase to connect. Further, even if the dynamic state of a subject becomes irregular during dynamic imaging, frame images taken while the dynamic state is not irregular can be used. This can prevent increase in the exposure dose to a subject.

Further, a phase width of the dynamic state to be obtained by imaging and a phase width of the dynamic state already obtained by the imaging device 1 are simultaneously displayed on the display unit 24. This lets a photographer readily catch how much the phase width of the dynamic state of valid frame images is already obtained (imaged) with respect to the phase width of the dynamic state to be obtained.

Further, when a complete set of frame images for the whole phase width of the dynamic state to be obtained by imaging is not present, the display unit 24 or the like displays information to lead a photographer to keep imaging the dynamic state (or outputs a predetermined sound or vibration therefor). This can prevent a photographer from stopping imaging halfway through the end.

Further, when a complete set of frame images for the whole phase width of the dynamic state to be obtained by imaging is not present, the display unit 24 or the like displays information to notify that an operation to proceed (a proceeding operation) to the next step is unavailable (or outputs a predetermined sound or vibration therefor). This can prevent proceeding to the next step without having a complete set of frame images for the whole phase width of the dynamic state to be obtained, the complete set of frames being necessary for diagnosis or analysis.

Further, when a complete set of frame images for the whole phase width of the dynamic state to be obtained by imaging is present, the display unit 24 or the like displays information to notify that the complete set of frame images is present (or outputs a predetermined sound or vibration therefor). This lets a photographer catch the imaging end timing.

In the above embodiments, the detection unit 211 detects the dynamic phase of a subject M based on image data of frame images. However, this is no limitation. For example, in the case of the subject M being a chest part, movement of the chest part or an abdomen part of the subject M may be detected with a respiration monitor belt, a surface pressure sensor, an acceleration sensor, a laser for ranging (distance measurement) or radio waves; respiratory airflow may be detected with an air flow meter; temperature change of nasal respiration may be detected with a temperature sensor or a far-infrared sensor; or movement of the chest part or the abdomen part may be detected by analyzing an image(s) obtained by projecting an image containing a reference line(s) to the subject M and imaging the subject M with a visible light camera, in parallel with radiation imaging. In addition to these, well-known respirometric methods can also be used.

Further, in the above embodiments, functions of the detection unit 211 and the change determination unit 212 are carried out by the CPU 21 of the imaging console 2, but may be carried out by a CPU (not shown) of the reading control device 14. In this case, it is unnecessary to, each time a frame image is obtained, send image data of the obtained frame image to the imaging console 2, and the image data may be sent with an arbitrary delay.

In addition to the above, detailed configurations and detailed actions of the devices or the like of the radiation imaging system 100 can also be appropriately modified without departing from the spirit of the present invention.

What is claimed is:

1. A radiation imaging system comprising:
   an imaging unit which emits radiation and images a dynamic state of a subject, thereby taking a plurality of frame images of the dynamic state of the subject;
   a detection unit which detects the dynamic state of the subject being imaged and generates detection information on the dynamic state;
   a change determination unit which determines whether change of the dynamic state being imaged is within a predetermined range based on the generated detection information; and
   a control unit which controls capturing of each individual frame image of the taken frame images according to a result of the determination of the change determination unit for the each individual frame image.

2. The radiation imaging system according to claim 1, wherein the change determination unit determines whether phase change of the dynamic state, as the change of the dynamic state, is within the predetermined range based on the generated detection information.

3. The radiation imaging system according to claim 1, wherein when the change determination unit determines that the change of the dynamic state is not within the predetermined range, the control unit discards up to a frame image determined by the change determination unit that the change of the dynamic state is not within the predetermined range, and captures a frame image, after the discarded frame image, determined by the change determination unit that the change of the dynamic state is within the predetermined range.

4. The radiation imaging system according to claim 1, wherein when the change determination unit determines that the change of the dynamic state is not within the predetermined range, the control unit discards a frame image determined by the change determination unit that the change of the dynamic state is not within the predetermined range, and automatically connects (i) a frame image taken by the imaging unit after the discarded frame image, determined by the change determination unit that the change of the dynamic state is within the predetermined range, and corresponding to a phase of the dynamic state, the phase being same as a phase of the dynamic state corresponding to the discarded frame image, to (ii) a frame image immediately before the discarded frame image.

5. The radiation imaging system according to claim 1, further comprising an operation unit through which connection command information to instruct frame images to connect is input, wherein
   when the change determination unit determines that the change of the dynamic state is not within the predetermined range, the control unit discards a frame image determined by the change determination unit that the change of the dynamic state is not within the predetermined range, and connects, based on the connection command information input from the operation unit, frame images other than the discarded frame image.

6. The radiation imaging system according to claim 4, further comprising a display unit which simultaneously displays a phase width of the dynamic state to be obtained by imaging and a phase width of the dynamic state already obtained by the imaging unit.

7. The radiation imaging system according to claim 4, further comprising an output unit which, when a complete set of frame images for a whole phase width of the dynamic state to be obtained by imaging is not present, outputs information to lead a photographer to keep imaging the dynamic state.

8. The radiation imaging system according to claim 4, further comprising an output unit which, when a complete set of frame images for a whole phase width of the dynamic state to be obtained by imaging is not present, outputs information to notify that an operation to proceed to a next step is unavailable.

9. The radiation imaging system according to claim 4, further comprising an output unit which, when a complete set of frame images for a whole phase width of the dynamic state to be obtained by imaging is present, outputs information to notify that the complete set of frame images is present.

10. The radiation imaging system according to claim 1, wherein the detection unit detects the dynamic state, the change determination unit determines whether change of the dynamic state being imaged is within a predetermined range, and the control unit controls capturing of each individual frame image while the imaging unit images the dynamic state of the subject.

11. A radiation imaging control device which controls an imaging device which emits radiation and images a dynamic state of a subject, thereby taking a plurality of frame images of the dynamic state of the subject, comprising:
   a detection unit which detects the dynamic state of the subject being imaged and generates detection information on the dynamic state;
   a change determination unit which determines whether change of the dynamic state being imaged is within a predetermined range based on the generated detection information; and
   a control unit which controls capturing of each individual frame image of the taken frame images according to a result of the determination of the change determination unit for the each individual frame.

12. The radiation imaging system according to claim 11, wherein the detection unit detects the dynamic state, the change determination unit determines whether change of the dynamic state being imaged is within a predetermined range, and the control unit controls capturing of each individual frame image while the imaging unit images the dynamic state of the subject.

13. A radiation imaging system comprising:
   an imaging unit which emits radiation and images a dynamic state of a subject, thereby taking a plurality of frame images of the dynamic state of the subject;
   a detection unit which detects the dynamic state of the subject being imaged and generates detection information on the dynamic state; and
   an operation unit through which connection command information to instruct, of the plurality of frame images, frame images to connect is input, wherein
   based on the connection command information input from the operation unit, the instructed frame images are connected, and frame images of the plurality of frame images that are not connected are discarded.

14. A radiation imaging system comprising:
   an imaging unit which emits radiation and images a dynamic state of a subject, thereby taking a plurality of frame images of the dynamic state of the subject;
   a detection unit which detects the dynamic state of the subject being imaged and generates detection information on the dynamic state;
   a change determination unit which determines whether change of the dynamic state being imaged is within a predetermined range based on the generated detection information;
   an operation unit through which connection command information to instruct, of the plurality of frame images, frame images to connect is input; and
   a control unit, which, when the change determination unit determines that the change of the dynamic state is not within the predetermined range, discards a frame image determined by the change determination unit that the change of the dynamic state is not within the predetermined range, and connects, based on the connection command information input from the operation unit, the instructed frame images other than the discarded frame image.

* * * * *